(12) United States Patent
Spoljaric

(10) Patent No.: US 7,762,635 B2
(45) Date of Patent: Jul. 27, 2010

(54) CABINET FOR FIRST-AID PRODUCTS

(75) Inventor: Davorin Spoljaric, Helsinki (FI)

(73) Assignee: Cederroth International AB, Upplands Vasby (SE)

( * ) Notice: Subject to any disclaimer, the term of this patent is extended or adjusted under 35 U.S.C. 154(b) by 447 days.

(21) Appl. No.: 11/795,492

(22) PCT Filed: Dec. 16, 2005

(86) PCT No.: PCT/SE2005/001941

§ 371 (c)(1),
(2), (4) Date: Jul. 18, 2007

(87) PCT Pub. No.: WO2006/078200

PCT Pub. Date: Jul. 27, 2006

(65) Prior Publication Data

US 2008/0111454 A1    May 15, 2008

(30) Foreign Application Priority Data

Jan. 20, 2005   (SE)   .................................... 0500145

(51) Int. Cl.
A47B 97/00    (2006.01)
A61F 17/00    (2006.01)

(52) U.S. Cl. ..................... 312/291; 312/245

(58) Field of Classification Search ............... 312/291, 312/292, 293.1–293.3, 326, 329, 209, 300, 312/308, 324, 245; 206/570, 523, 459.5, 206/370, 438, 572, 229, 803
See application file for complete search history.

(56) References Cited

U.S. PATENT DOCUMENTS

| | | | | |
|---|---|---|---|---|
| 489,593 A * | 1/1893 | Ramer | ........................ | 312/280 |
| 1,147,077 A * | 7/1915 | Collier | ........................ | 312/200 |
| 1,644,830 A * | 10/1927 | Henderson | ................... | 312/209 |
| 2,130,617 A * | 9/1938 | Dockham | .................... | 312/291 |
| 2,131,680 A * | 9/1938 | Zahodiakin | .................. | 62/266 |
| 2,150,064 A * | 3/1939 | Robert et al. | ................. | 62/266 |
| 2,656,948 A * | 10/1953 | Mcgee | ........................ | 220/3.8 |
| 2,671,623 A * | 3/1954 | Toulmin, Jr. | ............. | 244/138 R |
| 2,982,392 A * | 5/1961 | Bossone | ..................... | 224/400 |
| 3,140,134 A * | 7/1964 | Nairn | ......................... | 312/204 |
| 3,969,006 A * | 7/1976 | Brown | ..................... | 312/234.1 |

(Continued)

FOREIGN PATENT DOCUMENTS

CH    676792 A5    3/1991

(Continued)

Primary Examiner—Darnell M Jayne
Assistant Examiner—Timothy M Ayres
(74) Attorney, Agent, or Firm—Young & Thompson

(57) ABSTRACT

A cabinet (1) for first-aid products with an illustrated array of products distributed over and visible from a front side of the cabinet where the products can be easily grasped. The cabinet (1) includes a cabinet body (7) and two doors (2,3). A first door (2) to an inner space (4) of the cabinet (1) can be locked, the first door (2) includes openings (5) disposed to enable first-aid products to be taken out through the door (2). A second door (3) which is not lockable, is arranged on the outside of the first door (2) and the space (4) is intended to accommodate a store of first-aid products.

20 Claims, 5 Drawing Sheets

U.S. PATENT DOCUMENTS

| | | | |
|---|---|---|---|
| 4,861,305 A * | 8/1989 | Wilson | 446/75 |
| 5,401,093 A * | 3/1995 | Resnick | 312/234.1 |
| 5,484,196 A | 1/1996 | Kim | |
| 5,515,974 A * | 5/1996 | Higson | 206/570 |
| 6,382,746 B1 | 5/2002 | Rosas | |
| 6,454,097 B1 * | 9/2002 | Blanco | 206/570 |

FOREIGN PATENT DOCUMENTS

FR      2 589 340 A1    5/1987

\* cited by examiner

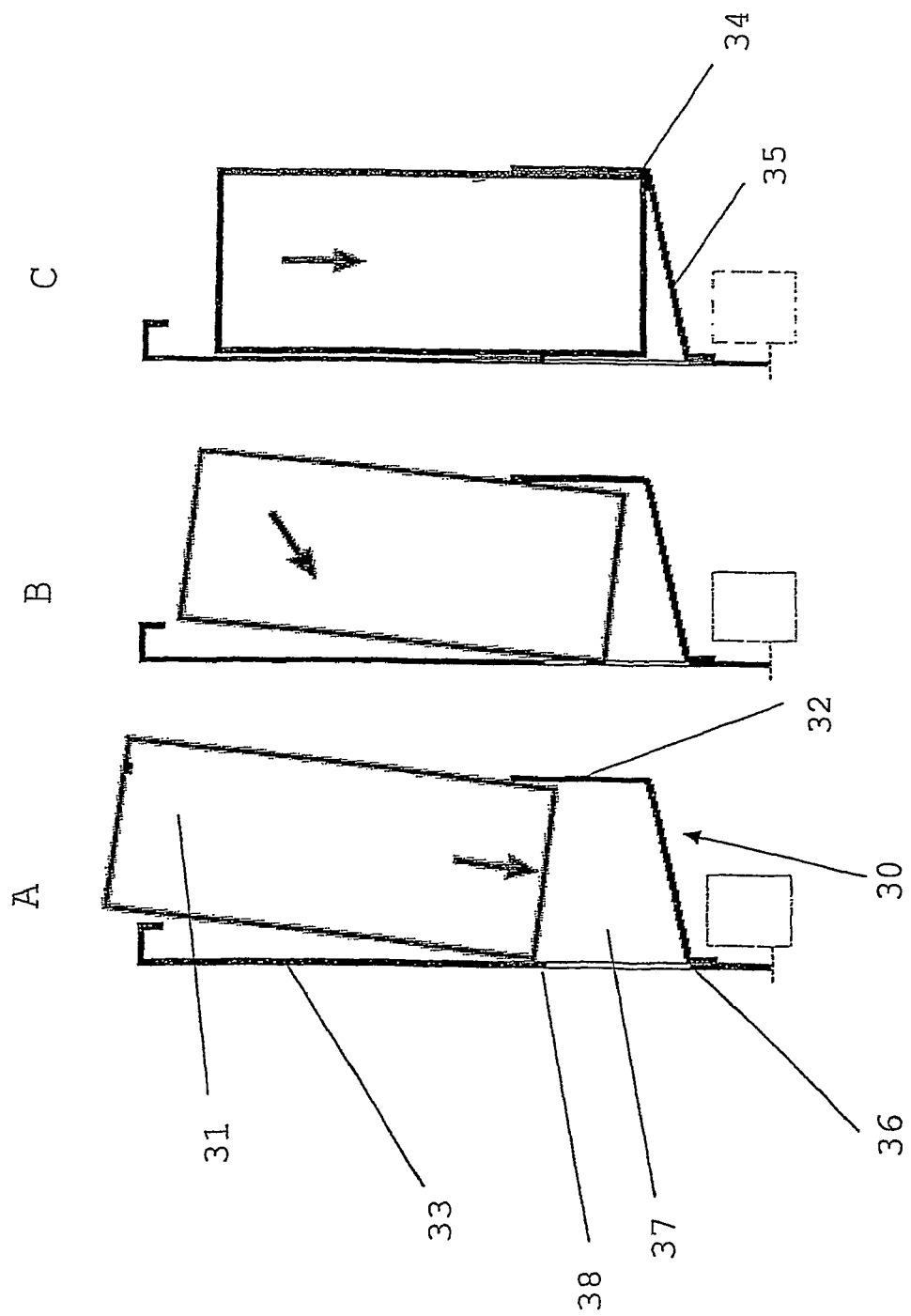

CABINET FOR FIRST-AID PRODUCTS

BACKGROUND OF THE INVENTION

1. Field of the Invention

The present invention-relates to a cabinet for first-aid equipment.

2. Description of Related Art

Workplaces, for instance, are today normally provided with first-aid equipment, such as first-aid boards or notices, first-aid cabinets or first-aid boxes, which are positioned so that personnel are able to find first-aid equipment quickly and easily in the event of an injury. Examples of products found in first-aid equipment include plasters, moist wipes, eye rinses, different sized bandages, masks, gloves and disinfection agents.

Different types of advanced first-aid equipment are also found. A first variant resides, for instance, in a first-aid board from Cederroth International AB, Sweden, which illustrates an array of first-aid products, such as those mentioned above, distributed over the board.

Another alternative is in the form of a metal cabinet that includes a protective door, also from Cederroth International AB, Sweden, in which a board is placed. The advantage with this second alternative is that the products are kept from being soiled by the surroundings, for instance by dust The protective door of the cabinet is fastened to the cabinet body by means of a magnetic fastener.

A third alternative is a cabinet in which a store of first-aid products included in said equipment is available, this cabinet also originating from Cederroth International AB, Sweden. The cabinet can be locked. An array of first-aid products is presented on the outside of the cabinet door.

It is desired to achieve primarily three important aspects with regard to one and the same product when concerned with first-aid equipments, in order for the products to fulfill their intended function.

According to a first aspect, it is utmost essential that the first-aid products can be accessed quickly and easily in the event of an accident or an injury.

According to a second aspect, it is important that the first-aid equipment can be readily replenished as soon as any of the first-aid products runs out without causing any undue problem, for instance that it is not well-known where the store of new products can be found. Consequently, it is necessary that the location of the products storage is close to hand in immediate connection with the first-aid equipment.

It may also happen that more of a first-aid product is required than is readily available in the first-aid equipment. The product store should be capable of being locked, so that personnel in the workplace are unable to take products therefrom. It is normal practice to entrust replenishment of the first-aid equipment to a responsible person in each working place.

SUMMARY OF THE INVENTION

All of these aspects are achieved by means of the present invention.

Accordingly, the present invention relates to a cabinet for first-aid products which has displayed on its front side an array of first-aid products and from which the products can be readily taken, wherein the invention is characterised in that the cabinet includes a cabinet body that has two doors; in that a first door leading to an inner space in the cabinet can be locked; in that the first door is provided with openings disposed so that first-aid products can be taken out through the door; in that a second non-lockable door is mounted outside the first door; and in that said space is intended to accommodate a store of first-aid products.

BRIEF DESCRIPTION OF THE DRAWING FIGURES

The invention will now be described in more detail partly with reference to exemplifying embodiments of the invention illustrated in the accompanying drawings, in which FIG. 1 is a diagrammatic illustration of a cabinet with both doors shown partially open;

FIG. 5 is a sectioned side view of a container for moist wipes, for instance.

DETAILED DESCRIPTION OF THE INVENTION

Figure 1:
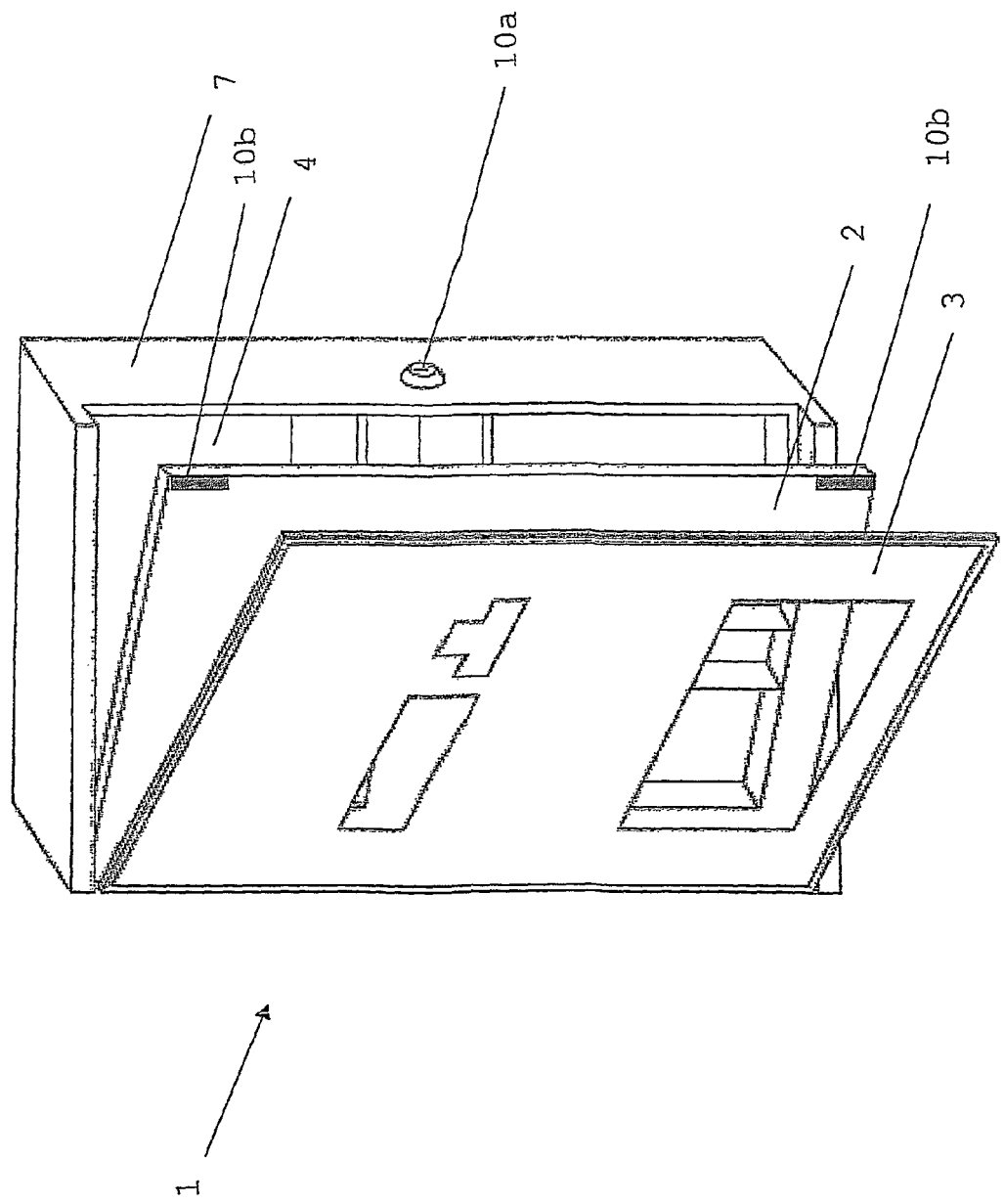

The present invention relates to a cabinet 1 for accommodating first-aid products, having an array of first-aid products distributed visibly on one front side of the cabinet 1 where the products can be readily grasped, as shown in FIG. 1.

According to the invention, the cabinet 1 includes a body 7 and two doors 2, 3. A first door 2 leads to an inner cabinet space 4 of the cabinet 1 and can be locked. The door 2 is conveniently lockable with the aid of a key lock 10a. The first door 2 is provided with openings 5 that are disposed so as to enable first-aid products to be taken out of the door 2. A second door 3, which is not lockable, is arranged outside the first door 2. The space 4 is intended to accommodate a store 40 of first-aid products, see FIGS. 1 and 2.

Although the second door 3 can have any desired appearance, it will preferably be transparent at least in those areas where the first-aid products are found placed in the first door 2, so that said products are clearly visible when the second door 3 is closed on the first door 2. When the second door 3 is not transparent, other markings may for example be made on the outside of the second door 3 in order to visualise to the user those products that are found inside the cabinet 1. For example, a picture can be taken of the first door 2 including its openings 5 with the first-aid products and fastened on the surface of the second door 3.

The first-aid products used are placed in respective containers 6 adapted for supporting respective first-aid products. These containers 6 are fastened to the inner surface of the first door 2 in connection with the openings 5. The containers 6 on the rear side of the first door 2 and the openings 5 in said first door are mutually spaced in relation to one another in a well-balanced fashion so that respective first-aid product refills, for instance a plaster package, will fit into its intended container 6 with the first-aid products well visible in the openings 5 on the front side of the first door 2.

Figure 4:
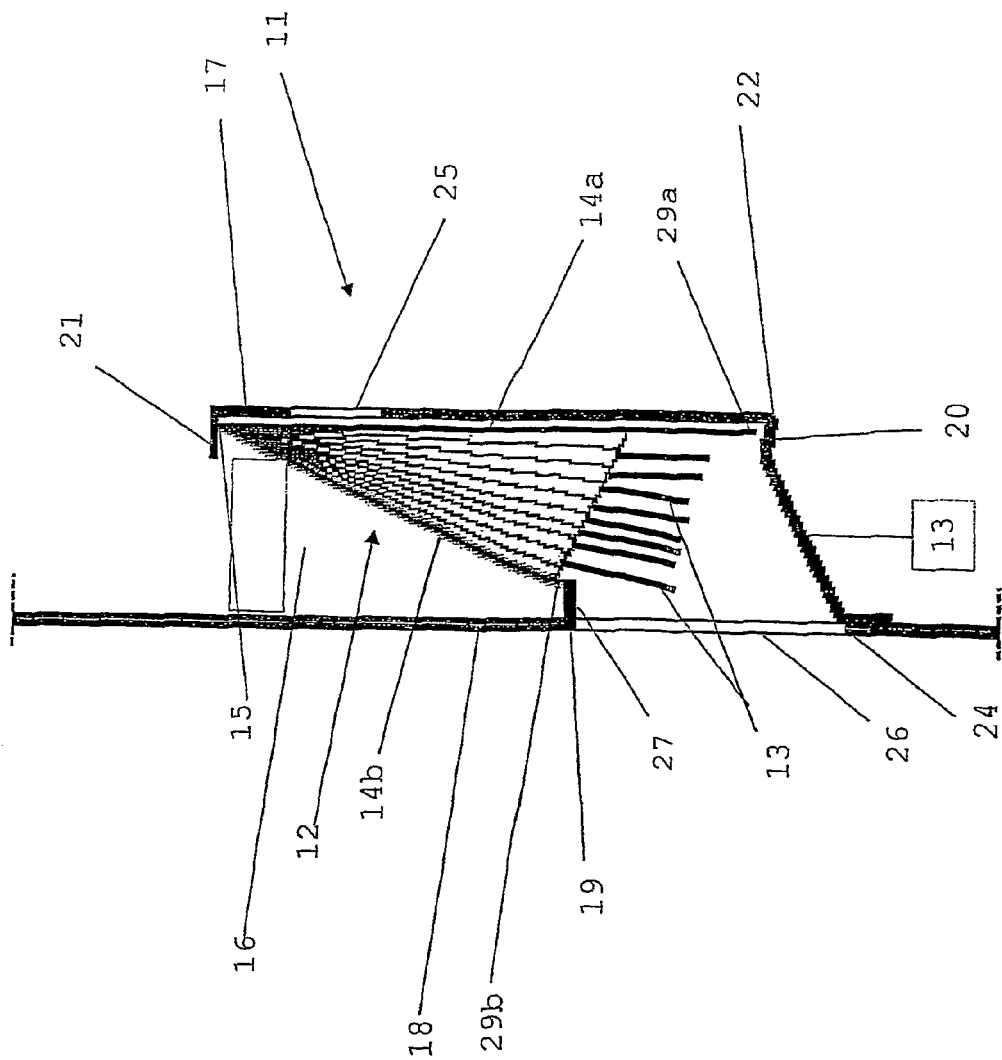
FIG. 4 is a sectioned side view of a plaster dispenser.

One of the containers will conveniently be a dispenser 11 which functions to dispense plasters 13 singly from a plaster pack 12 that includes a plurality of plasters 13, each accommodated in a plastic or paper pocket. The pockets are all directed in the same direction and are together surrounded by a folded sheet 14a, 14b of plastic or paper. The first edge 15 of the sheet extends at right angles to the longitudinal direction of the pockets. The plaster pack 12 is widened from said first edge 15 in a direction towards mutually opposing second edges 29a, 29b of the sheet parts 14a, 14b, where the plaster dispenser 11 includes a box-shaped space 16 as shown in FIG. 4.

The box-shaped space 16 is constructed in cross-section of two parallel and generally vertical walls. A rear wall 17 extends downwards in comparison with a front wall 18, wherein the rear wall 17 is lower than the bottom edge 19 of the front wall 18 at one height level and is configured with a rear generally horizontal shoulder 20. The upper edge of the rear wall 17 is folded so as to form a generally horizontal delimiting surface 21 and the distance between said delimiting surface 21 and said shoulder 20 corresponds to the width of the sheet 14a of the plaster pack 12 in a direction parallel with the longitudinal extension of the plaster pockets, see FIG. 4.

Another type of container may for example be one intended for accommodating for instance moist or wet wipes 30 that can be removed singly from a wipe pack 31 that includes a plurality of wipes placed in juxtaposed relationship in the pack 31; see FIG. 5.

The wipe container 30 is comprised in cross-section of two parallel and generally vertical walls. A rear wall 32 extends downwards in comparison with a front wall 33. In order to enable the rear wall 32 and the front wall 33 to be brought together, the rear wall 32 includes a planar part 35 which projects out from its lower edge 34 and which slopes downwards and outwards to the web plane 36 of the front wall. Also provided is an opening 37 formed in the front wall 33 between the lower edge 38 of the front wall 33 and the web plane 36 of the front wall 33 by a planar part 35 that projects out from the lower edge 34 of the rear wall 32, as shown in FIGS. 5A-5C.

The manner in which a wipe pack 31 is suitably placed down in the wipe container 30 is arrowed in FIGS. 5A-5C.

Another type of container 6 is for example one in which bandages or dressings of different sizes, masks, gloves and disinfection agents are placed piecewise in a specific container for removal therefrom.

The container for first-aid products has a box-like configuration and comprises a rear wall, four generally perpendicular walls having a respective first end which is placed against the periphery of the rear wall, wherein the first two of said four walls are generally parallel and vertical walls, whereas the remaining two walls are generally parallel with one another and horizontal, and generally perpendicular to the first two walls, wherein the other or second ends of the four walls opposite to the first ends of respective walls are placed against a front wall that extends generally parallel with and vertical to the rear wall. The front wall includes an opening through which access can be had to the box-shaped container from the opening in the front wall. The distance between the rear wall and the opening in the front wall is such as to enable the above mentioned products to be placed in a readily accessed position in the space intended therefor.

A common feature of the containers 6 described above is that they are formed on the rear side of the first door 2. When the first door 2 is closed against the cabinet body 7, only the first-aid products placed in the containers 6 can be reached.

Figure 2:
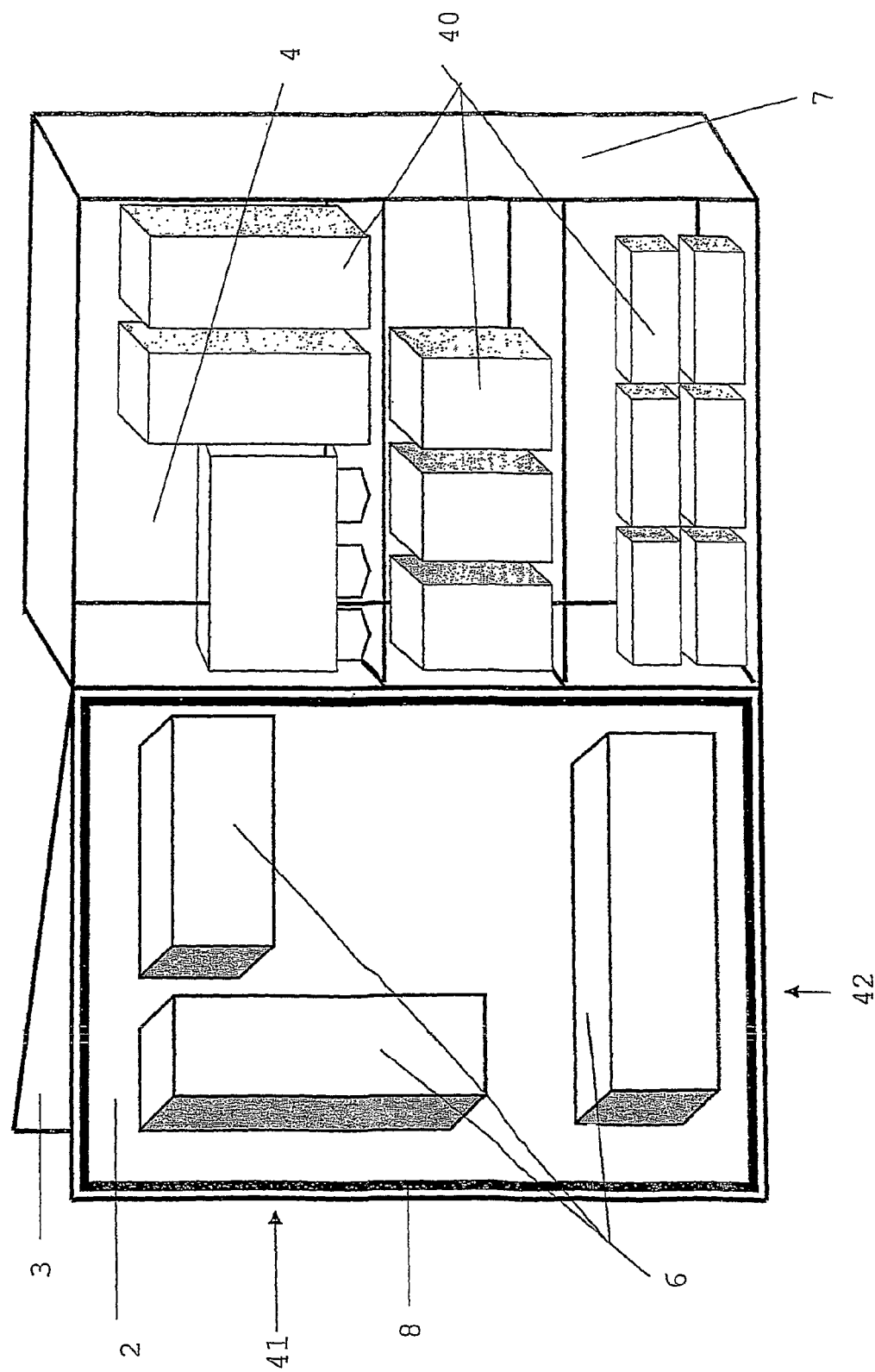
FIG. 2 illustrates a cabinet with a first and a second door fully open.

With the intention of obtaining an essentially dust-free cabinet 1 containing first-aid products and a space 4, a first seal 8 is provided at the periphery of the cabinet body 7 between said body and the first door 2. The first seal 8 may be placed on either one of the peripheral surfaces of the cabinet body 7 that faces towards the first door 2 or on the inner surface of the first door 2, or on both of the aforesaid surfaces, preferably along two long sides 41 and two short sides 42. In FIG. 2, the seal 8 is shown on the inner surface of the first door 2 facing towards the cabinet body 7. The first seal 8 will preferably be of the kind that is sufficiently ductile to enable it to be caused to abut essentially tightly against respective above mentioned surfaces of the cabinet body 7 and the first door 2.

Figure 3:
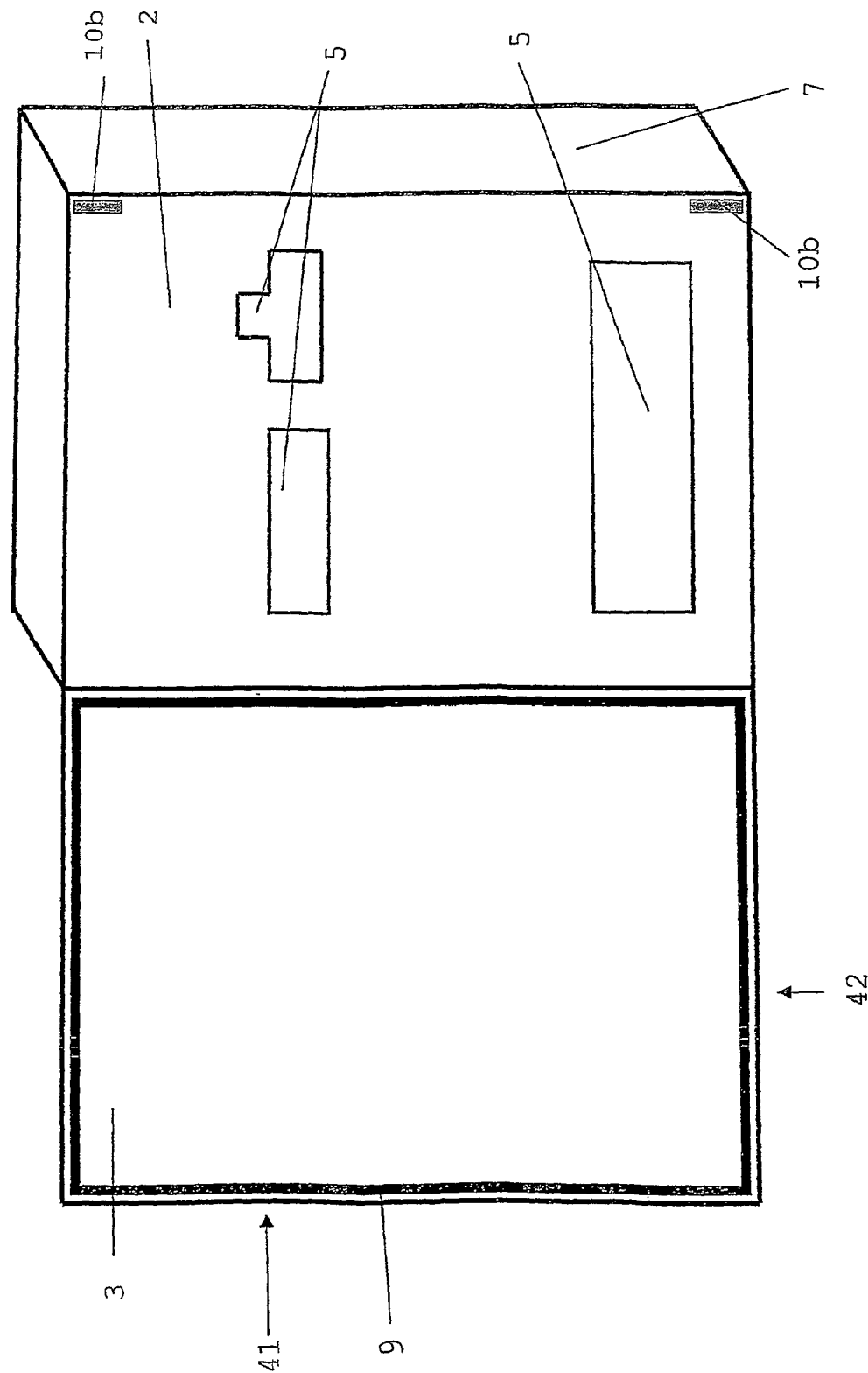
FIG. 3 illustrates a cabinet with a first door closed and a second door open.

The invention also includes the provision of a second seal 9 at the periphery of the first door 2, between said first door 2 and said second door 3. The second seal 9 may be placed on either one of the peripheral surfaces of the first door 2 that face towards the second door 3 or on the inner surface of the second door 3 or on both of said surfaces, preferably along two long sides 41 and two short sides 42. FIG. 3 shows the seal 9 on the inner surface of the second door 3 facing towards the first door 2. The second seal 9 should preferably be of the kind that is sufficiently ductile to enable it to be brought into generally tight abutment with the aforesaid respective surfaces of the first door 2 and the second door 3 so as to obtain a generally dust-proof seal.

According to one embodiment, the second seal 9 is placed solely on the inner surface of the second door 3 at two long sides 41 and short sides 42 of the door 3; see FIG. 3.

The first seal 8 may be of any suitable type whatsoever. According to one preferred embodiment, the first seal 8 has the form of a sealing strip. The second seal 9 also has the form of a sealing strip according to one embodiment.

The second door 3 can be held closed against the first door 2 with the aid of any appropriate means that does not require the provision of an external unit, for instance a key, in order to open the door 3. According to one preferred embodiment, the second door 3 is adapted to be held closed against the first door 2 by means of a locking device 10b, such as a magnetic lock or a padlock, for instance.

A combined number of desiderata are achieved by means of the unique cabinet 1. In addition to the design of the plaster pack 11, the remaining products are inserted in the first door 2 so as to be easily seen and readily accessed although locked-in nevertheless by virtue of the first door 2 being locked to the cabinet body 7. The first-aid products are also protected from contamination by the ingress of dust and moisture through the outer door 3, for instance.

Although a number of exemplifying embodiments have been described above, it will be understood that the first door 2, the second door 3, the first and the second seals 8, 9 and the magnetic lock 10 may have some other appropriate design without departing from the basic concept of the invention.

It will therefore be understood that the invention is not restricted to these exemplifying embodiments but that variations and modifications can be made within the scope of the accompanying Claims.

The invention claimed is:

1. A cabinet (1) and first-aid products that includes an illustrated array of first-aid products disposed on and visible from a front side of the cabinet (1) from where the products can be readily taken, comprising:
 a cabinet body (7) and two doors (2, 3);
 wherein a first door (2) to an inner space (4) of the cabinet (1) can be locked,
 said first door (2) includes openings (5) disposed to enable first-aid products to be taken out through the door (2),
 containers (6) are mounted on an inside of the first door (2) in connection with said openings (5), said containers (6) support the first-aid products, said containers (6) being mounted in such a way that only the first aid products placed in the containers can be reached,
 a second door (3), which is not lockable, is arranged on an outside of the first door (2), and
 said space accommodates a store of first-aid products.

2. The cabinet (1) and first-aid products in accordance with claim 1, wherein the second door (3) is transparent at least where the first-aid products are found placed in the first door (2), so that said first-aid products can be well-seen.

3. The cabinet (1) and first-aid products in accordance with claim 2, wherein a first seal (8) is disposed at a periphery of the cabinet body (7) between said body (7) and said first door (2).

4. The cabinet (1) and first-aid products in accordance with claim 2, wherein a first seal (8) is disposed at a periphery of the first door (2) between the cabinet body (7) and said first door (2).

5. The cabinet (1) and first-aid products in accordance with claim 2, wherein a second seal (9) is disposed at a periphery of the first door (2) between said first door (2) and said second door (3).

6. The cabinet (1) and first-aid products in accordance with claim 2, wherein a second seal (9) is disposed at a periphery of the second door (3) between said first door (2) and said second door (3).

7. The cabinet (1) and first-aid products in accordance with claim 1, wherein a first seal (8) is disposed at a periphery of the cabinet body (7) between said body (7) and said first door (2).

8. The cabinet (1) and first-aid products in accordance with claim 7, wherein the first seal (8) is a sealing strip.

9. The cabinet (1) and first-aid products in accordance with claim 1, wherein a first seal (8) is disposed at a periphery of the first door (2) between the cabinet body (7) and said first door (2).

10. The cabinet (1) and first-aid products in accordance with claim 9, wherein the first seal (8) is a sealing strip.

11. The cabinet (1) and first-aid products in accordance with claim 1, wherein a second seal (9) is disposed at a periphery of the first door (2) between said first door (2) and said second door (3).

12. The cabinet (1) and first-aid products in accordance with claim 11, wherein the second seal (9) is a sealing strip.

13. The cabinet (1) and first-aid products in accordance with claim 1, wherein a second seal (9) is disposed at a periphery of the second door (3) between said first door (2) and said second door (3).

14. The cabinet (1) and first-aid products in accordance with claim 13, wherein the second seal (9) is a sealing strip.

15. The cabinet (1) and first-aid products in accordance with claim 1, wherein the second door (3) is adapted to be held in a closed state relative to the first door (2) by means of a locking device (10b).

16. A cabinet and first-aid products, comprising:
an illustrated array of first-aid products disposed on and visible from a front side of the cabinet from where the products can be readily taken;
a cabinet body;
a lockable first door to an inner space of the cabinet, the lockable first door including openings disposed to enable the first-aid products to be taken out through the first door, said inner space being configured to accommodate a store of first-aid products;
an unlockable second door arranged on an outside of the first door; and
containers mounted on an inside of the first door in connection with said openings, said containers being adapted to support the first-aid products, said containers being mounted in such a way that only the first aid products placed in the containers can be reached.

17. The cabinet and first-aid products in accordance with claim 16, wherein the second door is transparent at least where the first-aid products are found placed in the first door, so that said first-aid products can be well-seen.

18. The cabinet and first-aid products in accordance with claim 16, wherein a first seal is disposed at a periphery of the cabinet body between said body and said first door.

19. The cabinet and first-aid products in accordance with claim 16, wherein a first seal is disposed at a periphery of the first door between the cabinet body and said first door.

20. The cabinet and first-aid products in accordance with claim 16, wherein a second seal is disposed at a periphery of the first door between said first door and said second door.

\* \* \* \* \*